(12) United States Patent
Duesterloh et al.

(10) Patent No.: US 11,224,563 B2
(45) Date of Patent: *Jan. 18, 2022

(54) TOPICAL COMPOSITIONS

(71) Applicant: DSM IP ASSETS B.V., Heerlen (NL)

(72) Inventors: Andre Duesterloh, Kaiseraugst (CH); Anne Janssen, Kaiseraugst (CH); Christeine Mendrok-Edinger, Kaiseraugst (CH); Karina Radomsky, Kaiseraugst (CH); Thomas Rudolph, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/312,575

(22) PCT Filed: Jun. 27, 2017

(86) PCT No.: PCT/EP2017/065891
§ 371 (c)(1),
(2) Date: Dec. 21, 2018

(87) PCT Pub. No.: WO2018/002073
PCT Pub. Date: Jan. 4, 2018

(65) Prior Publication Data
US 2019/0321277 A1    Oct. 24, 2019

(30) Foreign Application Priority Data

Jun. 27, 2016 (EP) .................................. 16176428
Jul. 1, 2016 (EP) .................................. 16177428

(51) Int. Cl.
*A61K 8/55* (2006.01)
*A61K 8/06* (2006.01)
*A61K 8/34* (2006.01)
*A61Q 17/04* (2006.01)
*A61Q 19/00* (2006.01)

(52) U.S. Cl.
CPC .............. *A61K 8/55* (2013.01); *A61K 8/062* (2013.01); *A61K 8/342* (2013.01); *A61Q 17/04* (2013.01); *A61Q 19/00* (2013.01)

(58) Field of Classification Search
None
See application file for complete search history.

(56) References Cited

U.S. PATENT DOCUMENTS

| 2,963,506 | A | | 12/1960 | Lewinski | |
|---|---|---|---|---|---|
| 5,455,037 | A | * | 10/1995 | Sakai | A61K 8/342 424/401 |
| 5,559,089 | A | | 9/1996 | Hartman et al. | |
| 2006/0069278 | A1 | * | 3/2006 | Stehr | C07F 9/11 558/117 |
| 2006/0171913 | A1 | * | 8/2006 | Schroder | A61K 8/062 424/70.23 |
| 2013/0095151 | A1 | | 4/2013 | Jawale et al. | |

FOREIGN PATENT DOCUMENTS

| CN | 102946848 | 2/2013 |
|---|---|---|
| KR | 20050100653 | 10/2005 |
| KR | 20140108328 | 9/2014 |
| WO | 01/62375 | 8/2001 |

OTHER PUBLICATIONS

Amphisol A, 2011 (Year: 2011).*
International Search Report for PCT/EP2017/065891, dated Aug. 11, 2017, 3 pages.
Croda,: "Croda Europe Ltd Cowick Hall Snaith Goole East", Sep. 1, 2014, 9 pages.
DSM: "Product Information Product Data Sheet—Amphisol® A", May 23, 2011, 2 pages.
DSM, "Product Information Product Data Sheet—Amphisol® K", Jun. 16, 2015, 3 pages.

* cited by examiner

*Primary Examiner* — Susan T Tran
*Assistant Examiner* — William Craigo
(74) *Attorney, Agent, or Firm* — Nixon & Vanderhye P.C.

(57) ABSTRACT

The present invention relates to topical composition comprising a cetyl phosphate surfactant mixture consisting essentially of mono- and/or dicetyl esters of phosphoric acid or salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

5 Claims, No Drawings

TOPICAL COMPOSITIONS

This application is the U.S. national phase of International Application No. PCT/EP2017/065891 filed 27 Jun. 2017, which designated the U.S. and claims priority to EP Patent Application No. 16176428.7 filed 27 Jun. 2016, and EP Patent Application No. 16177428.6 filed 1 Jul. 2016, the entire contents of each of which are hereby incorporated by reference.

The present invention relates to topical composition comprising a cetyl phosphate surfactant mixture consisting essentially of mono- and/or dicetyl esters of phosphoric acid or salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

'Cetyl phosphates', consisting essentially of mono- and/or dicetyl phosphate, cetyl alcohol and inorganic phosphate in varying amounts are widely used as surfactants in the cosmetic industry and are sold under the INCI 'Cetyl Phosphate'. The synthesis of highly effective cetyl phosphates from cetyl alcohol and phosphorous oxy chloride has been known for a long time. Such cetyl phosphates are e.g. commercially available under the Amphisol® brand at DSM Nutritional Products Ltd. This route however is getting less attractive because of the unavoidable formation of organochlorine impurities, such as in particular cetyl chloride. Thus, recently several chlorine-free cetyl phosphates prepared from cetyl alcohol and phosphorpentoxide or phosphoric acid have been brought to the market, which, however, exhibit formulation incompatibilities, in particular when formulating ethanol based product forms.

Thus, there is an ongoing need for a 'chlorine-free cetyl phosphate', i.e. a cetyl phosphate not containing organochlorine impurities such as in particular cetyl chloride which allows the formulation of ethanol based product forms, which remain stable over time. Such a cetyl phosphate should furthermore be obtainable in a sustainable and economical way avoiding e.g. the use of aromatic or halogenated solvents.

Surprisingly it has been found, that a specific 'chlorine-free cetyl phosphate', having an inorganic phosphate content of less than 0.7 wt.-% and a heavy metal content of less than 12 ppm allows the formulation of product forms, such as in particular ethanol based product forms, which remain stable over time.

Thus, in a first embodiment, the present invention relates to topical composition comprising a cetyl phosphate surfactant mixture consisting essentially of mono- and/or dicetyl esters of phosphoric acid or the respective salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

In particular the topical compositions contain the cetyl phosphate surfactant mixture as sole surfactant.

In a further embodiment, the topical compositions according to the present invention further contain an alcohol, preferably in an amount selected in the range of 0.5 to 20 wt.-%, more preferably in the range of 1 to 15 wt.-%, most preferably in the range of 5 to 10 wt.-%. The alcohol is preferably selected from the group consisting of $C_1$-$C_4$ alkyl alcohols such as in particular methanol, ethanol, n-propanol, isopropanol, 1-butanol, 2-butanol and tert.-butanol, $C_1$-$C_8$ alkyl diols such as in particular 1,2-hexanediol, 1,2- and 1,3-glycols such as in particular caprylylglycol, butylene and propyleneglycols, decylene glycol, phenols such as in particular meta, ortho or para-hydroxyacetophenone, butylhydroxytoluol (BHT), butylhydroxyanisole (BHA), o-cymen-5-ol, p-hydroxybenzoic acid $C_1$-$C_4$ esters and salicylates such as in particular ethylhexyl salicylate, homomenthyl salicylate, phenoxyethanol, benzyl alcohol, glycerin and ethylhexylglycerin as well as mixtures thereof.

In a particular advantageous embodiment the topical compositions according to the present invention contain ethanol, preferably in an amount selected in the range of 0.5 to 20 wt.-%, more preferably in the range of 1 to 15 wt.-%, most preferably in the range of 5 to 10 wt.-%, based on the total weight of the composition.

In another particular embodiment the topical compositions according to the present invention containing ethanol further contain phenoxyethanol and/or ethylhexylglycerine, preferably in an amount (total) selected in the range of 0.1 to 5 wt.-%, more preferably in the range of 0.25 to 3 wt.-%, most preferably in the range of 0.5 to 2 wt.-%, based on the total weight of the composition.

The term 'cetyl phosphate' as used herein refers to a mixture consisting essentially of mono- and dicetyl phosphate, cetylalcohol, inorganic phosphate, heavy metals, and residual water. Such surfactant mixtures are sold under the INCI name 'cetyl phosphate'.

The cetyl phosphate can be used in its free acid form, preferably however in all embodiments of the present invention, the cetyl phosphate is used as a salt with a cosmetically acceptable cation e.g. as diethanolamine or potassium salt, most preferably as potassium salt (i.e. as potassium cetyl phosphate).

Consequently, the term 'cetyl phosphate surfactant mixture' as used herein refers to a mixture consisting essentially of mono- and dicetyl phosphate (i.e. mono- and dicetyl esters of phosphoric acid or the respective salts thereof), cetylalcohol, inorganic phosphate, heavy metals and residual water.

The term 'inorganic phosphate' refers to the total amount of free phosphate ($PO_4^{3-}$) in the cetyl phosphate surfactant mixture as determined by means of the IC method. In a preferred embodiment, the total amount of the inorganic phosphate is less than 0.5 wt.-%, based on the total weight of the cetyl phosphate surfactant mixture. Consequently, it is well understood by a person skilled in the art, that the inorganic phosphate content in the topical compositions is accordingly preferably less than 0.05 wt.-%, based on the total weight of the topical composition.

The term 'heavy metal content' refers to the total amount of chromium, iron, antimony, arsenic, nickel and aluminum. The total amount of chromium, iron, antimony, arsenic, nickel and aluminum present in the cetyl phosphate surfactant mixture is determined by means of ICP-OES (e.g. at Solvias, Eurofins). In a preferred embodiment, the total amount of arsenic and aluminum in the cetyl phosphate surfactant mixtures according to the invention is, independently of each other, below 2 ppm, more preferably below 1 ppm.

The cetyl phosphate surfactant mixture can be used in its free acid form, i.e. containing mono- and dicetyl esters of phosphoric acid. Preferably however in all embodiments of the present invention, the cetyl phosphate surfactant mixture is used as a salt with a cosmetically acceptable cation e.g. as diethanolamine or potassium salt, most preferably as potassium salt (i.e. as potassium cetyl phosphate surfactant mixture i.e. containing the respective potassium salts of the mono- and dicetyl esters of phosphoric acid).

The amount of the cetyl phosphate surfactant mixture in the topical composition according to the present invention is preferably selected in the range of 0.1 to 10 wt.-%, more preferably in the range of 0.3 to 5 wt.-%, most preferably in the range of 0.5 to 3 wt.-%, based on the total weight of the topical composition.

Based on the above mentioned preferred amounts of the cetyl phosphate surfactant mixture, it is well understood to a person skilled in the art, that the topical compositions according to the present invention accordingly comprise preferably an amount of inorganic phosphate selected in the range of 0.0007 to 0.07 wt.-%, more preferably in the range of 0.0021 to 0.035 wt.-%, most preferably in the range of 0.0035 to 0.021 wt.-%, based on the total weight of the topical composition. Even more preferably, the inorganic phosphate content in the topical compositions according to the present invention is less than 0.01 wt.-% as this results in particularly stable compositions.

As the specific cetyl phosphate surfactant mixture as well as the respective salts thereof according to the present invention are still novel, the present invention also relates to a cetyl phosphate surfactant mixture, characterized in that the cetyl phosphate surfactant mixture consists essentially of mono- and dicetyl esters of phosphoric acid or a salt thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

In all embodiments according to the present invention, the cetyl phosphate surfactant mixture preferably consists essentially of 60-95 wt.-% of monocetyl phosphoric acid or a salt thereof, 0-15 wt.-% of dicetyl phosphoric acid or a salt thereof, 0-20 wt.-% of cetyl alcohol, 0-0.7 wt.-% of inorganic phosphate, 0-12 ppm of heavy metals and 0-4 wt.-% of residual water. More preferably, the cetyl phosphate surfactant mixture consists essentially of 70-90 wt.-% of monocetyl phosphoric acid or a salt thereof, 0.5-12 wt.-% of dicetyl phosphoric acid or a salt thereof, 0-15 wt.-% of cetyl alcohol, 0-0.7 wt.-% of inorganic phosphate, 0-12 ppm of heavy metals and 0-3 wt.-% of residual water. Most preferably the cetyl phosphate according to the present invention consists essentially of 70-85 wt.-% of monocetyl phosphoric acid or a salt thereof, 5-10 wt.-% of dicetyl phosphoric acid or a salt thereof, 7-12 wt.-% of cetyl alcohol, 0-0.5 wt.-% of inorganic phosphate, 0-11 ppm of heavy metals and 0-3 wt.-% of residual water.

Most preferably in all embodiments of the present invention the cetyl phosphate surfactant mixture is a potassium cetyl phosphate surfactant mixture consisting essentially of 72-85 wt.-% of monocetyl phosphate, 0.5-10 wt.-% of dicetyl phosphate, 0-15 wt.-% of cetyl alcohol, 7-12 wt.-% of potassium, 0-0.6 wt.-% of inorganic phosphate, 0-11 ppm of heavy metals and 0-2.5 wt.-% of residual water, even more preferably of 72-80 wt.-% of monocetyl phosphate, 5-10 wt.-% of dicetyl phosphate, 7-12 wt.-% of cetyl alcohol, 7-12 wt.-% of potassium, 0-0.5 wt.-% of inorganic phosphate, 0-10 ppm of heavy metals and 0-2.5 wt.-% of residual water.

The term 'consisting essentially of' as used according to the present invention means that the total amount of the listed ingredients ideally sums up to 100 wt.-%. It is however not excluded that small amount of impurities derived from the production process may be present, with the proviso however, that no organochlorine impurities are present.

In another preferred embodiment of the present invention, the ratio (w/w) of mono- and dicetyl esters of phosphoric acid or salts thereof in the cetyl phosphate surfactant mixture according to the present invention is selected in the range of 170 to 1, preferably in the range of 20 to 5, most preferably in the range of 15 to 8.

The residual water content is to be understood as determined by Karl Fischer titration (e.g. described in Eugen Scholz Karl-Fischer-Titration, Springer-Verlag 1984 or the WHO Method WHO/M/7.R1).

The term 'chlorine-free' as used herein refers to a cetyl phosphate surfactant mixture which is substantially free (i.e. below limit of detection) of organochlorine impurities such as in particular of cetyl chloride. In a preferred embodiment, the term 'chlorine-free' refers to a cetyl phosphate surfactant mixture prepared via a route not employing any phosphorous oxy chloride, halogenated reagents or halogenated solvents, by which means the formation of organochlorine impurities such as in particular cetyl chloride is per se avoided.

The cetyl phosphate surfactant mixture according to the present invention is preferably prepared by reacting cetyl alcohol with pyrophosphoric acid in hexane and/or cyclohexane, preferably cyclohexane, at a reaction temperature of about 60 to 90° C., preferably 70 to 85° C. followed by hydrolysis with water resulting in the respective mixture of mono- and dicetyl esters of phosphoric acid, cetyl alcohol, inorganic phosphate, heavy metals and residual water. The ratio (mol) of pyrophosphoric acid to cetyl alcohol is preferably selected in the range of 5 to 1, more preferably in the range of 4 to 2, most preferably in the range of 3.5 to 2.5.

The present invention accordingly also relates to cetyl phosphate surfactant mixtures obtained by the process according to the present invention.

The respective salts are prepared by standard methods in the art e.g. by reacting the free acids with a base releasing a cosmetically acceptable cation such as e.g. with an aqueous solution of potassium hydroxide.

A particular suitable cetyl phosphate surfactant mixture according to the present invention is commercially available as Amphisol® L at DSM Nutritional products Ltd.

The compositions according to the invention are intended for topical application, which is to be understood as the external application to keratinous substances, such as in particular the skin.

As the compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically acceptable carrier.

The term 'cosmetically acceptable carrier' as used herein refers to a physiologically acceptable medium which is compatible with keratinous substances. Suitable carriers are well known in the art and are selected based on the end-use application. Suitable carriers can include one or more compatible liquid or solid filler diluent, excipient, additive or vehicle which are suitable for application to skin surhair. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The compositions according to the present invention are in a form suitable for the application to the skin such as e.g. sunscreens, creams, milks, lotions, masks, serums, hydrodispersions, foundations, creamgels, or gels etc. or to hair, in particular eyelashes, such as e.g. mascara.

In accordance with the present invention, the compositions according to the invention may also comprise further cosmetically active ingredients conventionally used in cosmetic and/or pharmaceutical compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The topical compositions according to the present invention are typically prepared by admixing the cetyl phosphate surfactant mixture according to the present invention with suitable excipients, diluents, adjuvants and/or additives. If desired, active ingredients can additionally be added to the topical compositions according to the present invention.

Thus, the invention also relates to a process for the preparation of a topical composition according to the present invention, said process comprising the step of admixing a cetyl phosphate surfactant mixture according to the present invention with a cosmetically acceptable carrier.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The compositions according to the present invention preferably are in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

In a particular advantageous embodiment, the compositions according to the present invention are in the form of an oil-in-water (O/W) emulsion comprising an oily phase dispersed in an aqueous phase in the presence of a cetyl phosphate surfactant mixture according to the present invention. The preparation of such O/W emulsions is well known to a person skilled in the art. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

The compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The following examples are provided to further illustrate the compositions and effects of the present invention. These examples are illustrative only and are not intended to limit the scope of the invention in any way.

EXAMPLES

A: Preparation of a Chlorine-Free Cetyl Phosphate Surfactant Mixture According to the Present Invention 0.09 mol of cetyl alcohol is added into a flask and diluted with 20 ml of cyclohexane and heated to 75° C. Afterwards 0.3 mol of pyrophosphoric acid diluted in 30 ml of cyclohexane is slowly added. After the addition is complete the reaction is stirred for another hour at 75° C. Afterwards water is added and the reaction stirred for 15 min at 70° C. Then the water phase is separated and the organic phase is washed twice with water followed by removal of cyclohexane in vacuo. The thus obtained crude product is neutralised with 10 g of 50% KOH in water at 50° C. Then methanol is added and the crystallized product is filtered off. The resulting product is recrystallized from methanol resulting in 10 g of a cetyl phosphate surfactant mixture according to the present invention (corresponding to Amphisol® L).

1. Analytics 1.1. Method for the Determination of Monocetylphosphate by Titration 1.5 g (+/−0.1 g) of the respective homogenized potassium cetylphosphate (powder) was weighed into a 150 mL Erlenmeyer flask with stopper. 60 mL of isopropanol/water mixture (20/80, v/v) was added. The suspension was stirred at 80° C. for 30 min in a closed flask. The solution was titrated at 70° C. on a heatable magnetic stirrer using 0.5 M sodium hydroxide solution as titrant.

1.2. Method for the Determination of Monocetylphosphate and Cetylalcohol by GC-FID 3-4 mg (+/−0.01 mg) of the respective homogenized potassium cetylphosphate (powder) was weighted into a 2 mL GC-Vial. 1 mL of a solution prepared by dissolving 140 mg tricosane (internal standard) in a 200 ml flask in 100 mL N,O-bis(trimethylsilyl)-trifluoroacetamide with 1% trimethylchlorosilane and pyridine (to 200 ml volume)) was added. The GC vial was closed and vortexed for 10 sec, followed by heating the vial for 20 min at 120° C. and vortexing the hot GC vial for another 10 sec. After cooling to RT, the samples were subjected to GC analysis in triplicates. (Column: Optima 5 HT, 30 m×0.25 mm 0.1 μm, Hydrogen flow rate: 2.2 mL/min (constant flow), Oven programme: 200° C. (0 min) Ramp to 360° C. (20° C./min), 360° C. (0 min)).

1.3. Method for the Determination of Dicetylphosphate by FIA-MS 100 mg (+/−0.01 mg) of the respective homogenized potassium cetylphosphate (powder) was weighted into a 100.0 ml glass volumetric flask. Then, 50.0 ml of tetrahydrofuran/water (70/30, v/v) was added and the mixture was sonicated for dissolution. The volume was adjusted with tetrahydrofuran/water (70/30, v/v). Then, 1 ml of this solution was diluted with an ammonium carbonate solution (300 mg ammonium carbonate in 100 ml water and 900 ml methanol) to 100 ml. Afterwards the amount of dicetyl phosphate was analyzed by FIA-MS (HPLC-MS Agilent 1260, No column, T=40° C., 5 μl, Detector: ESI-MS)

The amount of dicetyl phosphate in the sample was calculated using an external calibration with dicetyl phosphate.

1.3. Method for the Determination of Inorganic Phosphate 0.25 g of the respective homogenized potassium cetylphosphate was weighed into a 100 mL volumetric flask. After the addition of 90 mL THF/Water (70/30, v/v) the flask was placed in an ultrasonic bath for dissolution. Afterwards, the flask was filled to volume with THF/Water (70/30, v/v). 1 mL of this solution was pipetted into a 10 mL flask and filled up to volume with demineralised water. The samples were then analyzed in triplicates by IC chrompatography (Dionex ICS-3000, Chromatographic data system: Chromeleon, Detector: CD-3000 conductivity detector, Column: AS19 column (4.0 mm×250 mm) protected with an AG19 precolumn (4.0 mm×50 mm), Eluent: KOH gradient (0-55 mmol), injection volume 25 μl).

TABLE 1

Analytical results of various chlorine-free potassium cetyl phosphate surfactant mixtures

| Sample | Inv | Ref-1 | Ref-2 | Ref-3 |
|---|---|---|---|---|
| Monocetyl phosphate (wt.-%) | 75# | 79.64# | 47* | 73.6# |
| Dicetyl phosphate wt.-(%) | 6.8 | 10.1 | 11 | 22.5 |
| Inorganic phosphate (wt.-%) | 0.34 | 2.12 | 16.78 | 0.54 |
| Cetylcohol (wt.-%) | 9.1 | 0.5 | 6.1 | 1.7 |
| heavy metals sum ppm | 8.0 | 12.1 | 23.1 | 23.0 | via Titration;
*via GC-FID
(potassium cetyl phosphate surfactant mixtures: Inv: Amphisol ® L, Ref-1: EverMap 160K by Sino Lion, Ref-2: Crodafos MCK by Croda, Ref-3: Romol AFSK by Suzhou Eleco Chemical Industry Co. Ltd)

2. Formulation

The formulations as outlined in table 2 were prepared using the different potassium cetyl phosphate surfactant mixtures outlined in table 1. After storage at 22° C. for 3 months, the respective samples were assessed visually for their appearance. As can be retrieved from the results outlined in table 3, only the cetyl phosphate surfactant mixture according to the present invention led to stable formulations over the whole range.

TABLE 2

| | INCI | Formulation 1 | 2 | 3 | 4 wt.-% | 5 | 6 | 7 |
|---|---|---|---|---|---|---|---|---|
| A | Cetyl alcohol | 2.00 | 2.00 | 2.00 | 2.00 | 2.00 | 2.00 | 2.00 |
| | C$_{12-15}$Alkyl Benzoate | 15.00 | 15.00 | 15.00 | 15.00 | 15.00 | 15.00 | 15.00 |
| | Potassium cetyl phosphate surfactant mixture according to table 1 | 2.00 | 2.00 | 2.00 | 2.00 | 2.00 | 2.00 | 2.00 |
| B | Aqua | | | | Ad 100 | | | |
| | Xanthan Gum | 0.15 | 0.15 | 0.15 | 0.15 | 0.15 | 0.15 | 0.15 |
| | Glycerin | 3.00 | 3.00 | 3.00 | 3.00 | 3.00 | 3.00 | 3.00 |
| C | Phenoxyethanol & Ethylhexylglycerine | 1.00 | 1.00 | 1.00 | 1.00 | 1.00 | 1.00 | 1.00 |
| D | Ethanol (EtOH) | 0.00 | 3.00 | 5.00 | 8.00 | 10.00 | 13.00 | 15.00 |

TABLE 3

Stability data in dependence of the EtOH concentration after 3 months storage @ RT (~22° C.)

| # | EtOH wt.-% | Inv | Ref-1 | Ref-2 | Ref-3 |
|---|---|---|---|---|---|
| 1 | 0 | OK | OK | OK | OK |
| 2 | 3 | OK | OK | OK | OK |
| 3 | 5 | OK | OK | phase separation | OK |
| 4 | 8 | OK | OK | phase separation | OK |
| 5 | 10 | OK | OK | phase separation | OK |
| 6 | 13 | OK | phase separation | phase separation | OK |
| 7 | 15 | OK | phase separation | phase separation | phase separation |

The invention claimed is:

1. A topical composition, wherein the composition is an oil-in-water (O/W) emulsion of an oil phase dispersed in an aqueous phase, the composition comprising:
    (a) 5-15 wt. %, based on total weight of the topical composition, of ethanol, and
    (b) 0.5 to 3 wt. %, based on the total weight of the topical composition, of a potassium cetyl phosphate surfactant mixture, wherein the potassium cetyl phosphate surfactant mixture consists of, based on total weight of the surfactant mixture:
        (i) 70-90 wt. % of a potassium salt of monocetyl phosphate,
        (ii) 0.5-12 wt. % of a potassium salt of dicetyl phosphate,
        (iii) 0-15 wt. % of cetylalcohol,
        (iv) 0-0.7 wt. % of an inorganic phosphate,
        (v) 0-12 ppm of heavy metals, and
        (vi) 0-3 wt. % of residual water, wherein
        the surfactant mixture contains no organochlorine impurities, and wherein
    the topical composition does not exhibit phase separation after storage for 3 months at a temperature of about 22° C.

2. The topical composition according claim 1, wherein the potassium cetyl phosphate surfactant mixture consists of:
    72-85 wt. % of the potassium salt of monocetyl phosphate,
    0.5-10 wt. % of the potassium salt of dicetyl phosphate, 0-15 wt. % of the cetyl alcohol,
7-12 wt. % of potassium,
0-0.6 wt. % of the inorganic phosphate,
0-11 ppm of the heavy metals, and
0-2.5 wt. % of the residual water.

3. The topical composition according to claim 1, which further comprises:
   (c) 0.1 to 5 wt. %, based on the total weight of the topical composition, of phenoxyethanol and/or ethylhexlyglycerine.

4. The topical composition according to claim 1, which further comprises:
   (c) 0.25 to 3 wt. %, based on the total weight of the topical composition, of phenoxyethanol and/or ethylhexlyglycerine.

5. The topical composition according to claim 1, which further comprises:
   (c) 0.5 to 2 wt. %, based on the total weight of the topical composition, of phenoxyethanol and/or ethylhexlyglycerine.

\* \* \* \* \*